US008282920B2

(12) United States Patent
Heo et al.

(10) Patent No.: US 8,282,920 B2
(45) Date of Patent: Oct. 9, 2012

(54) **PHAGE THERAPY AGAINST *PSEUDOMONAS AERUGINOSA***

(75) Inventors: Yun-Jeong Heo, Seoul (KR); Yu-Rim Lee, Mungyeong Gyeongsangbuk-Do (KR); Hyun-Hee Jung, Seoul (KR); You-Hee Cho, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 146 days.

(21) Appl. No.: 12/579,242

(22) Filed: Oct. 14, 2009

(65) Prior Publication Data

US 2010/0209349 A1 Aug. 19, 2010

(30) Foreign Application Priority Data

Feb. 17, 2009 (KR) ........................ 10-2009-0012659

(51) Int. Cl.
*A01N 63/00* (2006.01)
*A61K 39/40* (2006.01)
*A61K 39/00* (2006.01)
*A61K 45/00* (2006.01)
*A61K 39/108* (2006.01)
*C12N 15/00* (2006.01)

(52) U.S. Cl. ................. 424/93.6; 424/170.1; 424/184.1; 424/278.1; 424/260.1; 435/320.1

(58) Field of Classification Search ........................ None
See application file for complete search history.

(56) References Cited

U.S. PATENT DOCUMENTS

2005/0244383 A1* 11/2005 Sulakvelidze et al. ....... 424/93.6

OTHER PUBLICATIONS

Hagens et al., 2004. "Therapy of experimental *Pseudomonas* infections with a nonreplicating genetically modified phage." *Antimicrob Agents Chemother* 48:3817-22.
Matsuzaki et al., 2005. "Bacteriophage therapy: a revitalized therapy against bacterial infectious diseases." *J Infect Chemother* 11:211-9.
McVay et al., 2007. "Phage therapy of *Pseudomonas aeruginosa* infection in a mouse burn wound model." *Antimicrob Agents Chemother* 51:1934-8.
Smith et al., 1983. "Effectiveness of phages in treating experimental *Escherichia coli* diarrhoea in calves, piglets and lambs." *J Gen Microbiol* 129:2659-75.
Smith et al., 1987. "The control of experimental *Escherichia coli* diarrhoea in calves by means of bacteriophages." *J Gen Microbiol* 133:1111-26.
Summers et al., 2001. "Bacteriophage therapy." *Annu Rev Microbiol* 55:437-51.
Watanabe et al., 2007. "Efficacy of bacteriophage therapy against gut-derived sepsis caused by *Pseudomonas aeruginosa* in mice." *Antimicrob Agents Chemother* 51:446-52.

* cited by examiner

*Primary Examiner* — Vanessa L. Ford
*Assistant Examiner* — Lakia Tongue
(74) *Attorney, Agent, or Firm* — Edwards Wildman Palmer LLP

(57) ABSTRACT

This invention relates to a bacteriophage MPK6 (deposit number: KCCM 11044P) having a lytic activity to *Pseudomonas aeruginosa*, or a progeny bacteriophage thereof having a RFLP (Restriction fragment length polymorphism) DNA profile substantially equivalent to the bacteriophage MPK6. The present invention provides a bacteriophage MPK6 or a progeny bacteriophage thereof capable of treating a *Pseudomonas aeruginosa* infection disease, and suggests an anti-bacterial activity of MPK6 and its progeny bacteriophage using a mammalian and non-mammalian infection model. According to the present invention, the present bacteriophage MPK6 or progeny bacteriophage thereof represents very effective efficacy on treatment of *P. aeruginosa*-induced peritonitis-sepsis.

4 Claims, 6 Drawing Sheets

MPK6

PHAGE THERAPY AGAINST *PSEUDOMONAS AERUGINOSA*

CROSS-REFERENCE TO RELATED APPLICATIONS

This application claims priority from Korean Patent Application No. 2009-0012659, filed on Feb. 17, 2009, the disclosure of which is incorporated herein by reference.

BACKGROUND

1. Technical Field

The present invention relates to a bacteriophage MPK6 and a progeny bacteriophage thereof, and a pharmaceutical composition for treating a *Pseudomonas aeruginosa* infection disease.

2. Background Art

*Pseudomonas aeruginosa* is an opportunistic human pathogen that is ubiquitously found in various biotic and abiotic environments. It is frequently isolated from human patients afflicted with cystic fibrosis, otitis media, kertatitis, and burn wound infections, as an etiological agent of septicemia in immunocompromised individuals. This bacterium, generally from the environmental reservoir, can colonize a large numbers of child patients before the age of 3 years, and adversely affect their pulmonary function (28, 33). Furthermore, *P. aeruginosa* is also commonly found in peritonitis-sepsis cases secondary to ruptured appendices in otherwise healthy children (4). Peritonitis by *P. aeruginosa* is a serious threat also to the patients undergoing continuos ambulatory peritoneal dialysis (CAPD) (17), accounting for 10% of fatality cases associated with CAPD. The bacterial intoxication usually leads to high morbidity, CAPD failure, and late complications in those cases (16, 17, 19). Rodent models of *P. aeruginosa* peritonitis have been developed for understanding the pathophysiology implicated in peritonitis (38). The pathological consequences generally accompany bacteremia and infected livers with serum levels of interleukin-6 elevated within 6 h post-infection and ultimately cause mortality within 48 hours depending on *P. aeruginosa* strains and infection doses (5).

Although antibiotics have still been widely used to control the bacterial infections, they are more frequently ineffective due to the inevitable emergence of antibiotic resistance. Selection and dissemination of intrinsic and acquired antibiotic resistance mechanisms increase the proclivity to resist the chemotherapy involving various antibiotics and promote the emergence of bacterial strains with multiple antibiotic resistances, which are associated with the mortality and morbidity in infected patients nowadays (26, 34). Hence, development of new therapeutic and prophylactic strategies is compulsory in the control of the bacterial infections.

As an alternative and/or supplementary antiinfective modality for combating infections caused by antibiotic-resistant microorganisms, which is currently being revisited in various countries, is bacteriophages that are able to specifically target their host bacterial infections, which is called phage therapy (35). Phage therapy is a method of harnessing phages as bioagents and was first introduced by Felix d'Herelle back in 1916, before the discovery of the first antibiotic, penicillin (36). Phages continue to be used in place of antibiotics for the treatment of bacterial infections in the former Soviet Union and the Eastern Europe (30). Much more attention has recently been paid to phage therapy, as more and more bacteria have very rapidly evolved antibiotic resistance. Thus phage therapy may be a valuable alternative modality to antibiotics and has already been proven to be medically superior to antibiotics in certain cases (3, 22).

*P. aeruginosa* is a highly adaptable bacterium that enhances its ecological fitness even in the presence of conventional antibiotic therapy. The rapid emergence of new *P. aeruginosa* strains as well as the persistence of the existing antibiotic-resistant clinical isolates has led to an urgent need to explore more sustainable alternative strategies such as phage therapy to manage *P. aeruginosa*-mediated infections. Recently, the efficacy of phage therapy using a genetically modified filamentous phage (Pf3R) (10), lytic phage isolates or phage cocktails has been investigated against various experimental mouse infection models by *P. aeruginosa* that include burn wound infection (23) and gut-derived sepsis (37). Because the pathophysiology caused by *P. aeruginosa* infections is quite complicated, more and more relevant infection models need to be tested for the efficacy and relevancy of the antibacterial therapies.

The above information disclosed in this Background section is only for enhancement of understanding of the background of the invention and therefore it may contain information that does not form the prior art that is already known in this country to a person of ordinary skill in the art.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have intensive studies to develop a bacteriophage therapy for treating a *Pseudomonas aeruginosa* infection disease, for example, *Pseudomonas aeruginosa-induced* peritonitis. As results, we have discovered that MPK6 (Accession number: KCCM 11044P) as a novel bacteriophage belonging to be a order Caudovirales conferred resistance to mouse peritonitis-sepsis induced by an intraperitoneal infection of *P. aeruginosa* strain, PAO1, and MPK6 and its progeny bacteriophage had an anti-bacterial activity using a mammalian and non-mammalian infection model.

Accordingly, it is an object of the invention to provide a bacteriophage MPK6 or a progeny bacteriophage thereof.

It is another object of this invention to provide a pharmaceutical composition for treating a *Pseudomonas aeruginosa* infection disease.

It is still another object of this invention to provide a method for treating a *Pseudomonas aeruginosa* infection disease.

It is still another object of this invention to provide a method for screening antibiotics against *Pseudomonas aeruginosa*.

Other objects and advantages of the present invention will become apparent from the detailed description to follow taken in conjugation with the appended claims and drawings.

BRIEF DESCRIPTION OF THE DRAWINGS

FIGS. 5A-5B show mortality of PAO1-infected mice with and MPK6 (squares; □ and ■) at MOI of 1 (open symbols; □) or 10 (solid symbols; ■), which were administered by the i.m. (A) or i.p. route (B) at 6 h post-infection. PAO1-infected mice without phage treatment (◇) were 100% moribund within 48 h. The statistical significance based on logrank test: , p<0.01; *, p<0.001. FIG. 5C represents bacterial burdens in lung, spleen, and liver of mice treated with or without intraperitoneal phage treatment as in B at MOI of 10. The numbers of viable bacteria (CFU) were measured from the organs of live mice at 24 h post-infection. The CFU per unit volume (ml) were measured as described in Materials and Methods and are shown in a log scale. Symbols: no phage treatment, ◇; MPK6, □.

FIG. 6A is pharmacokinetics of MPK1 and MPK6. Phage samples ($5 \times 107$ 536 PFU in PBS) of either MPK1 (A; ○ and ●) or MPK6 (B; □ and ■) were overlaid on the surface of the fly media. Groups of flies (n=5) were collected at 0.5, 12, 24, 36, and 48 h and their homogenates were removed to measure the PFU per fly, which is shown in a log scale. FIG. 6B represents mortality of PAO1-infected flies fed with phages. Infected flies were transferred to a new medium overlaid with nothing (◇) or phage samples ($5 \times 10^7$ PFU in PBS) of either MPK1 (●) or MPK6 (■). The dotted line represents the time required to reach the 50% mortality. The statistical significance based on logrank test: ***, p<0.001. FIG. 6C shows bacterial burdens in fly homogenates fed with phages as in A. The number of viable bacteria (CFU) was measured from the homogenates of an individual live (open symbols) and dead (solid symbols) fly at 0.5 h, 12 h, 24 h, or 48 h post-infection. The CFU per fly are shown in a log scale. Symbols: no phage treatment, ◇ and ◆; MPK1, ○ and ●; MPK6, □ and ■.

DETAILED DESCRIPTION

Figure 1:
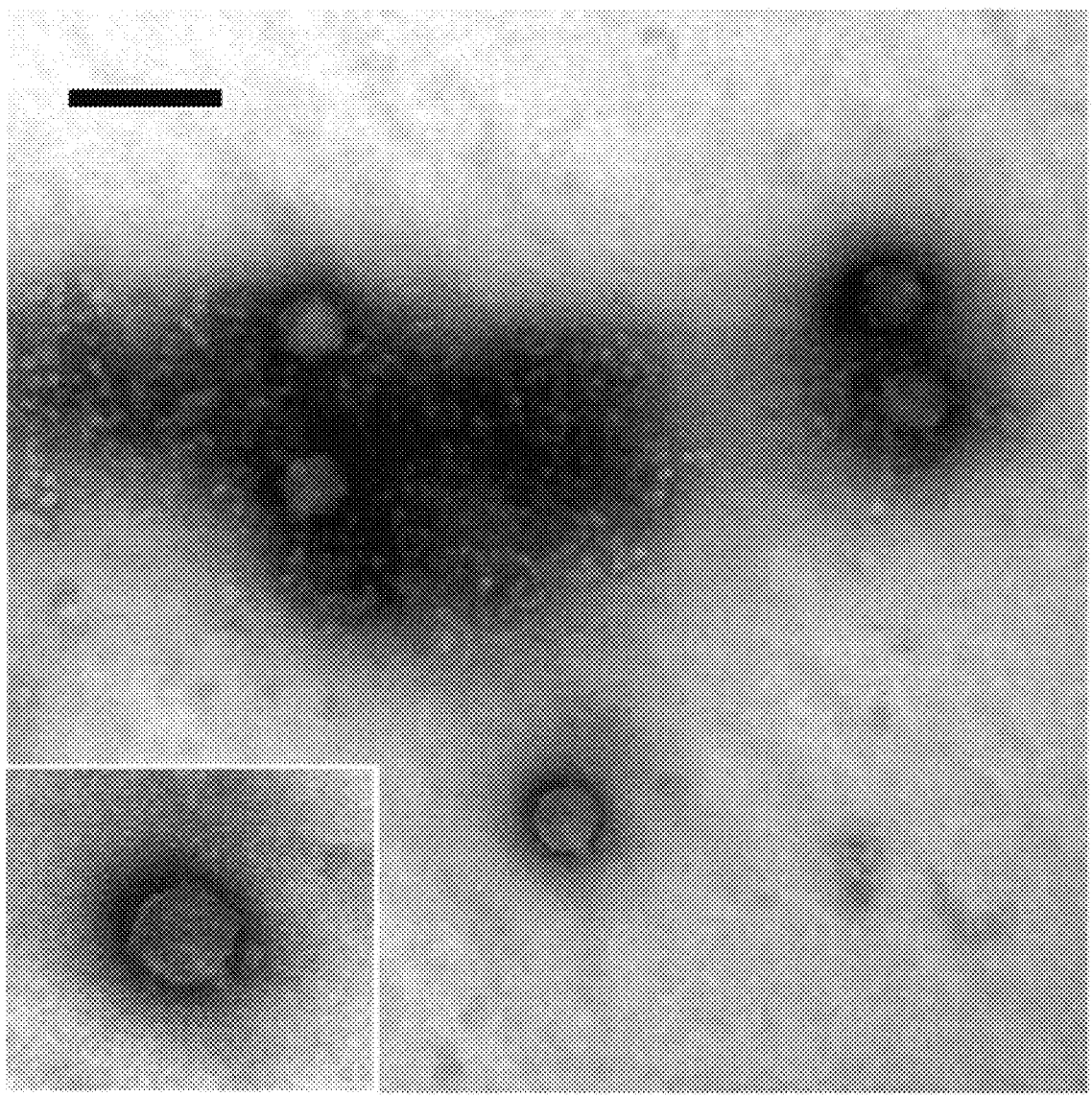
FIG. 1 represents transmission electron micrographs of MPK6 negatively stained with uranylacetate revealing their virion structure. Bar 100 nm.

In one aspect of this invention, there is provided a bacteriophage MPK6 (deposit number: KCCM 11044P) having a lytic activity to *Pseudomonas aeruginosa*, or a progeny bacteriophage thereof having a RFLP (Restriction fragment length polymorphism) DNA profile substantially equivalent to the bacteriophage MPK6.

In another aspect of this invention, there is provided a pharmaceutical composition for treating a *Pseudomonas aeruginosa* infection disease, comprising: (a) a therapeutically effective amount of the bacteriophage; and (b) a pharmaceutically acceptable carrier.

In still another aspect of this invention, there is provided a method for treating a *Pseudomonas aeruginosa* infection disease, which comprises administering to a subject the pharmaceutical composition comprising the bacteriophage.

In further still another aspect of this invention, there is provided a method for screening antibiotics against *Pseudomonas aeruginosa*.

The present inventors have intensive studies to develop a bacteriophage therapy for treating a *Pseudomonas aeruginosa* infection disease, for example, *Pseudomonas aeruginosa*-induced peritonitis. As results, we have discovered that MPK6 (Accession number: KCCM 11044P) as a novel bacteriophage belonging to be a order Caudovirales conferred resistance to mouse peritonitis-sepsis induced by an intraperitoneal infection of *P. aeruginosa* strain, PAO1, and MPK6 and its progeny bacteriophage had an anti-bacterial activity using a mammalian and non-mammalian infection model.

Bacteriophage is a bacteria virus which internally replicates via a complicated lytic cycle and lyses a host cell through bacteria lysis. This characteristics of phage is very specific in the senses that the phages attack bacteria as their targets. However, the utilization of phage has been gradually reduced because the phage is safe but has a short spectrum to pathogens compared to antibiotics having a broad spectrum capable of effectively conferring resistance to a variety of pathogens. Recently, the phage therapy has been newly focused according to high understanding about the phage. Although the phage has been practically used in various therapies containing the treatment of various diseases in many animals, the isolation of a novel phage, the selection of an optimal phage for a practical application in a specific manner, and the development of a method utilizing phage have been urgently demanded in several fields containing clinic application, safety-related use and improvement of environment contaminations. In addition, a novel phage and its identification method are necessarily demanded for preventing or treating a bacteria-induced disease, disorder or condition in human and animal (i.e., a disease induced by antibiotics-resistant bacteria).

According to the present invention, the bacteriophage MPK6 (deposit number: KCCM 11044P) or the progeny bacteriophage thereof having a RFLP (Restriction fragment length polymorphism) DNA profile substantially equivalent to the bacteriophage MPK6 has a strong lytic activity to bacteria (e.g., *Pseudomonas aeruginosa*).

*Pseudomonas aeruginosa* is a gram-negative bacterium belonging to Proteobacteria. Proteobacteria include *Salmonella, Shigella* and Enterobacteriaceae, *Pseudomonas, Moraxella, Helicobacter, Stenotrophomonas, Bdellovibrio*, a-proteobacteria, and so on. In medicine, Proteobacteria induces a respiratory disease by *Hemophilus influenzae, Klebsiella pneumoniae, Legionella pneumophila* or *Pseudomonas aeruginosa*, an urinary disorder by *Escherichia coli, Proteus mirabilis, Enterobacter cloacae* or *Serratia marcescens*, a gastrointestinal system disorder by *Helicobacter pylori, Salmonella enteritidis* or *Salmonella typhi*.

*Pseudomonas aeruginosa* exists in several living or non-living environments, and is a pathogen arisen when the human immune system is alleviated. *Pseudomonas aeruginosa* may infect hosts derived from multiple backgrounds such as plant, worm and insect.

According to a preferable embodiment, the *Pseudomonas aeruginosa* infection disease treated by the present pharmaceutical composition includes cystic fibrosis, otitis media, keratitis, endophthalmitis, bacteremia, burn wound infection, pneumonia, meningitis, peritonitis or sepsis, more preferably pneumonia, meningitis, peritonitis or sepsis, and most preferably peritonitis or sepsis.

According to this invention, the novel bacteriophage MPK6 or its progeny bacteriophage isolated in the present invention may treat the *Pseudomonas aeruginosa* infection disease.

The term "progeny" referred to a novel phage MPK6 herein means bacteriophage replicates containing descendents produced according to subculture of the deposited bacteriophage or a method known to those ordinarily skilled in the art, or bacteriophages having a RFLP (Restriction fragment length polymorphism) DNA profile substantially equivalent to the deposited bacteriophage. The term "have a substantially equivalent or equal RFLP" is expressed to represent a variability between organisms according to the method suggested by Tenover et al. (Tenover, F. C. et al. Interpreting Chromosomal DNA Restriction Patterns Produced by Pulsed-Field Gel Electrophoresis: Criteria for Bacterial Strain Typing. *J. Clin. Microbiol* 33:2233-2239 (1995)). Tenover et al. suggest an acceptable level of variability with a proviso that genome of identical propagated organisms is restricted with restriction enzymes and then electrophoresized. According to the standard suggested by Tenover et al, a progeny having an equivalent RFLP DNA profile may be considered as a bacteriophage substantially equivalent to the bacteriophage MPK6.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition.

The pharmaceutical composition according to the present invention may be administered orally or parenterally, and preferably, administered parenterally, e.g., by intravenous, intra-abdominal, intramuscular, intraperitoneal or transdermal. Preferably, the pharmaceutical composition of the present invention may be administered with a daily dosage of $10^1$-$10^{10}$ PFU/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

According to the present invention, the present invention provides a method for screening antibiotics against *Pseudomonas aeruginosa*, comprising the steps of:

(a) infecting *Pseudomonas aeruginosa* to *Drosophila melanogaster*, (b) administrating a substance of interest to the infected *Drosophila melanogaster*, and (c) measuring a morality of the infected *Drosophila melanogaster* or a CFU (colony forming unit) of a lysate of the infected *Drosophila melanogaster*.

Based on that a set of virulence factors identified from a *Drosophila melanogaster* systemic infection-based screen are also required for mouse peritonitis (18), we here first established a *D. melanogaster* model to evaluate the phage therapy and verified the antibacterial efficacy of both MPK1 and MPK6 (Accession number: KCCM 11044P) using this non-mammalian infection model.

The present inventors first established a *D. melanogaster* model as a screening method for identifying a novel antibiotics against *Pseudomonas aeruginosa* to prevent or treat a *Pseudomonas aeruginosa* infection disease in human and animals.

According to a preferable embodiment, the *Pseudomonas aeruginosa* in the step (a) is used at 10-1000 CFU, more preferably 20-700 CFU, much more preferably 30-400 CFU and most preferably 50-200 CFU for infection. Thus, it is advantageous that the present invention could perform the screening in an effective manner because the infection number of *Pseudomonas aeruginosa* used in the present invention is quite small.

The administration of the substance interested to be screened may be carried out orally (e.g., primarily intestinal injection by feeding) or parenterally (e.g., directly pricking or injecting into a body region such as dorsal thorax), and preferably parenterally.

According to a preferable embodiment, the step (a) is carried out by direct injection of *Pseudomonas aeruginosa* into dorsal thorax of *Drosophila melanogaster*.

According to a preferable embodiment, the step (b) is performed by administrating the substance of interest to the infected *Drosophila melanogaster* via an oral route.

According to the method of the present invention, the morality of the for infected *Drosophila melanogaster* or a CFU (colony forming unit) of a lysate of the infected *Drosophila melanogaster* is finally measured to screen antibiotics against *Pseudomonas aeruginosa*.

A test substance is evaluated to have a lytic activity to *Pseudomonas aeruginosa* where the treatment of the test substance may reduce the morality or the CFU of a lysate of the *Drosophila melanogaster* infected with *Pseudomonas aeruginosa*. As results, the test substance is determined as a candidate having a potential for treating a *Pseudomonas aeruginosa*-infection disease.

According to a preferable embodiment, the substance of interest includes a single compound, a mixture or a phage and more preferably a phage.

The test substance analyzed according to the present screening method may be obtained from libraries of synthetic or natural compounds, or natural substances. The method to prepare the library of such compounds is well known in the art. The library of synthetic compounds may be commercially purchased from Maybridge Chemical Co. (UK), Comgenex (USA), Brandon Associates (USA), Microsource (USA) and Sigma-Aldrich (USA) and the library of natural compounds may be commercially purchased from Pan Laboratories (USA) and MycoSearch (USA).

The test substance may be obtained from various combination library methods known to those ordinarily skilled in the art, for example, including a spatially addressable parallel solid phase or solution phase library method, a synthetic library method in which deconvolution is required, a "1-bead 1-compound" library method, and a synthetic library method using an affinity chromatography for selection. The synthetic method of molecule library is disclosed in DeWitt et al., *Proc. Natl. Acad. Sci. U.S.A.* 90, 6909, 1993; Erb et al., *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; and Gallop et al., *J. Med. Chem.* 37, 1233, 1994.

The features and advantages of this invention are summarized as follows:

(a) The present invention provides a bacteriophage MPK6 or a progeny bacteriophage thereof capable of treating a *Pseudomonas aeruginosa* infection disease.

(b) The present invention suggests an anti-bacterial activity of MPK6 and a progeny bacteriophage thereof using a mammalian and non-mammalian infection model.

(c) According to the present invention, the present bacteriophage MPK6 or progeny bacteriophage thereof represents very effective efficacy on treatment of *P. aeruginosa*-induced peritonitis-sepsis.

The present invention relates to a screening method for inhibitors of cancer cell invasion and a screening system thereof. According to the screening system and screening method using the same, the inhibitor to cancer cell invasion is able to be screened in a high-throughput manner.

EXAMPLES

Experimental Materials and Methods

Bacterial Strains and Culture Conditions

*Pseudomonas aeruginosa* strain PAO1 was used as described elsewhere (12). The lipopolysaccharide mutants (rmd, wbpM, and rmlC) are gifted from Dr. Joe Lam (University of Guelph, Canada). Bacterial cells were grown in Luria-Bertani (LB; 1% triptone, 0.5% yeast extract and 1% NaCl) broth with aeration or 2% Bacto-agar (Difco) LB or cetrimide agar (Pseudomonas isolation agar, Fluka) plates at 37° C.

Preparation of Phage Lysates

Phage strains MPK1 and MPK6 are enriched by plate lysate method using *P. aeruginosa* strain PAO1 as the host as described elsewhere (13). The culture suspension was centrifuged at 8,000×g for 10 min at 4° C. to remove the cell debris, and the phage particles were precipitated from culture supernatant in the presence of 10% polyethylene glycol (average molecular weight, 8,000) and 1 M NaCl, and then dissolved in 5 ml phage buffer [10 mM $MgSO_4$, 10 mM Tris (pH 7.6), and 1 mM EDTA]. Phage particles were concentrated by ultracentrifugation at 110,000×g for 3 h at 4° C., resuspended in phage buffer. The phage suspension was placed on top of a discontinuous CsCl gradient (1.45, 1.50, 1.70 g/ml) and centrifuged at 87,000×g for 2 h at 4° C. The phage band was collected and dialyzed.

Transmission Electron Microscopy

The virion morphology of phages MPK1 and MPK6 was determined by transmission electron microscopy (TEM) as described previously (13). Briefly, formvar-coated TEM grids were subjected to hydrophilic treatment (10 min) and floated with 1/100 diluted CsCl-purified phage samples (20 µl) immediately followed by negative staining (5 sec) using 20 µl of 2% uranyl acetate (pH 4.0). The grids were allowed to air-dry for 30 min and examined under a transmission electron microscope (JEM 1010 EM; JEOL Ltd) at 120~500 K magnification.

Phage Infection

Phage infection is observed either by conventional plaque assay or spotting assay (12). For plaque assay, 10 µl of lysates that contain about $10^2$ plaque forming unit (PFU) phages were mixed with $10^7$ colony forming unit (CFU) of *P. aeruginosa* cells grown to the late logarithmic growth phase [i.e., the optical density at 600 nm ($OD_{600}$) of 0.7] and resuspended in 100 µl of phage buffer. After 10 min incubation, 3 ml of top agar was added and the mixture was plated. Plaques were visualized after 16~24 h of incubation at 37° C.

Mouse Experiments

Mouse infection was carried out using female ICR mice (aged 4 weeks), following the protocol approved by the Animal Care and Use Committee at Sogang University. Bacterial cells were grown to the stationary growth phase ($OD_{600}$ of 3.0), harvested, washed twice with phosphate buffered saline (PBS) buffer (2.7 mM KCl, 137 mM NaCl, 10 mM $Na_2HPO_4$, and 2 mM KH2PO4, pH 7.0) and then resuspended in PBS buffer at $2\times10^7$ CFU/ml. To induce peritonitis, mice were infected intraperitoneally with 100 µl of the bacterial suspension (i.e., $2\times10^6$ CFU). We did not use 10% mucin in this experiment. For phage therapy, after 6 to 12 h post-infection, phage solution containing either $2\times10^6$ [i.e., multiplicity of infection (MOI) of 1] and $2\times10^7$ (MOI of 10) PFU in PBS buffer (100 µl) was administered either intraperitoneally or intramuscularly. For enumeration of bacterial burden from mouse tissues, infected mice were anaesthetized by inhalation of ether at the designated time points (0.5, 12, 24, 36, and 48 h post-infection). Lung, liver, and spleen samples were obtained aseptically and homogenized with a tissue homogenizer (Yamato Scientific Co., Ltd., Tokyo, Japan) in PBS buffer (1 ml). Portions of blood and homogenized tissue samples were plated onto cetrimide agar, which were incubated for 24 h at 37° C. For phage pharmacokinetics, phages were administered either intraperitoneally or intramuscularly into the uninfected mice, from which the blood, lung, and liver samples were obtained and homogenized at the designated time points (0.5, 12, 24, 36, and 48 h). The tissue homogenates were subjected to filtration and the filtrates were used for PFU measurement by plaque assay.

*Drosophila melanogaster* Experiments

*Drosophila melanogaster* Oregon R was grown at 25° C. using the corn meal-dextrose medium [0.93% agar, 6.24% dry yeast, 4.08% corn meal, 8.62% dextrose, 0.1% methyl paraben, and 0.45% (v/v) propionic acid], as described elsewhere (20), with slight modification. Briefly, Infection of flies was performed by picking 5 day old adult flies in the dorsal thorax with a 10-µm needle (Ernest F Fullam). The needle was dipped halfway into PBS-diluted bacterial suspension containing $10^7$ CFU/ml from the stationary growth phase ($OD_{600}$ of 3.0) cultures. At this dilution, we introduced 50-200 bacteria/animal. Infected flies were transferred to a new medium overlaid with 100 µl phage solution containing $5\times10^7$ PFU. Fly mortality was monitored for up to 48 h post-infection. Flies that died within 15 h in this condition (less than 5%) were not included in mortality determination. Mortality studies were repeated at least five times. For enumeration of bacterial burdens, infected flies were anaesthetized by $CO_2$ and ground in LB at the designated time points. Homogenates of individual infected flies were plated onto LB agar, which were incubated at 37° C. for 24 h to measure the CFU per fly. For phage pharmacokinetics in *D. melanogaster*, phages were fed for 12 h and the flies were transferred to a new medium without phage. Flies were homogenized at the designated time points (0.5, 12, 24, 36, and 48 h) and the tissue homogenates were filtered and the filtrates were used for PFU measurement by plaque assay.

Statistical Analysis

Kaplan-Meier logrank statistics was used to determine the statistical significance of the differences between the control and the treatment groups in mortality rates. The statistical significance in the numbers of viable bacteria recovered from blood and organs were verified by the Mann-Whitney U test.

Results

Identification of the New Caudovirales Phage Strains for *P. aeruginosa*

Phages specific to *P. aeruginosa* strains were initially isolated from sewage samples, which have been obtained several times in Seoul and the suburban districts. Once isolated, phages were screened for their lytic activity on the basis of large and distinguishable plaque formation, a characteristic of lytic phages. The present inventors selected 6 potentially lytic phages for *P. aeruginosa* strain PAO1 (named as MPK1 to MPK6), based on the plaque size (over 3 mm diameter after 18 h incubation at 37° C.) and clarity (data not shown; see FIG. 2). The present inventors determined the morphology of those 6 phages by using transmission electron microscope. Based on their virion structure, MPK1 to MPK5 belongs to the Myoviridae family (order Caudovirales), with the icosahedral head of ~70 nm diameter and the contractile tails of ~110 nm length with fibers (data not shown; FIG. 1A). In contrast, MPK6 has a similar head as MPK1, but with a stubby tail of less than 10 nm length (FIG. 1B) and thus belong to morphotype C, subdivision C1 of the Podovindae family (order Caudovirales) (1, 2, 8). Conclusively, the present inventors have isolated 6 Caudovirales phages, which are most likely lytic for *P. aeruginosa*. The present inventors selected MPK1 from the Myoviridae phages and MPK6 for the next experiments. Of both, MPK6 had been deposited on Jan. 21, 2009 in International Depository Authority, the Korean Culture Center of Microorganisms and was given accession number KFCC 11438P and has been converted to International Deposit on Oct. 12, 2009 and given accession number KCCM 11044P.

Receptor of Phages MPK6

A number of surface receptors on *P. aeruginosa* have been implicated as bacteriophage receptors. Especially, the type IV pili (TFP) have been shown to function as the primary receptors for various *P. aeruginosa* phages including filamentous phage Pf (6), single stranded RNA phage PP7 (8), Bradley B-type phage PO4 (7) and temperate transducing phages such as MP22 (13).

Figure 2:
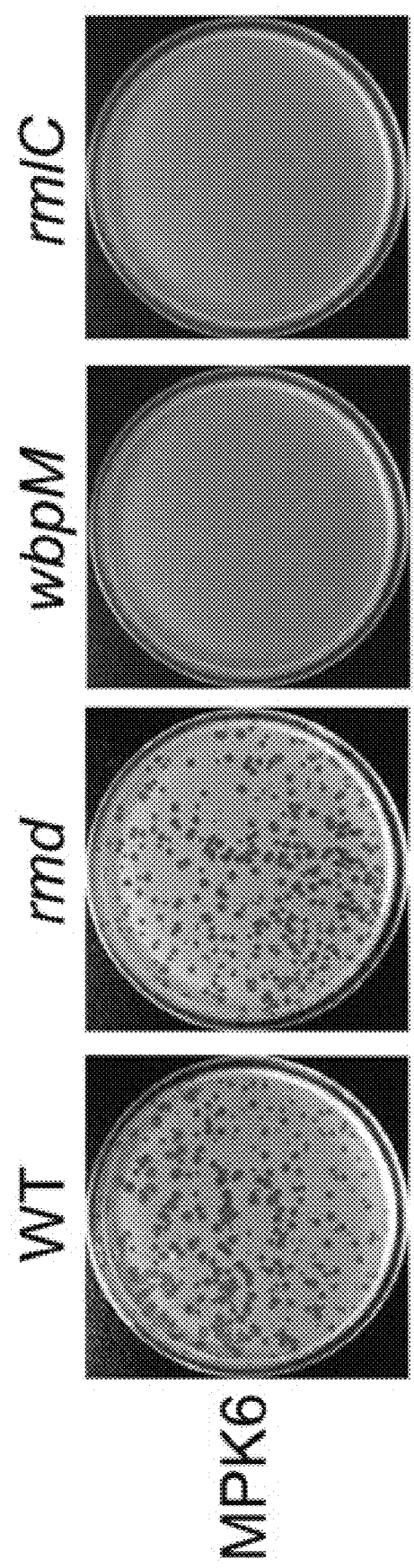
FIG. 2 represents a plaque formation by MPK6 on various lipopolysaccharide (LPS) mutants. MPK6 phage lysates containing about $3\times10^2$ PFU were spotted onto the bacterial lawns of PAO1 (WT) and its congenic LPS mutants: rmd ($A^-B^+core^+$), wbpM ($A^+B^-core^+$), and rmlC($A^-B^-core^-$).

The candidate is lipopolysaccharide (LPS), although detailed molecular components in the LPS as the phage receptors remain elusive. Only the LPS core region is known to act as the phage receptor for phi PLS27 (15) and phi CTX (39). To determine whether LPS might act as the receptor for MPK1 and MPK6, the present inventors used a series of LPS mutants derived from PAO1 strain: rmd (deficient for A-polysaccharide), wbpM (deficient for B-polysaccharide), and rmd (deficient for core-polysaccharide and hence for A- and B-polysaccharide as well). As shown in FIG. 2, whereas both phages could form clear plaques on the wild-type and rmd bacteria, no plaques were formed on rmlC bacteria. Therefore, the LPS B-polysaccharide is most likely the primary receptors for the phage MPK6 entry into the PAO1 cells.

Lytic Activity of Phages MPK6 In Vitro

Figure 3:
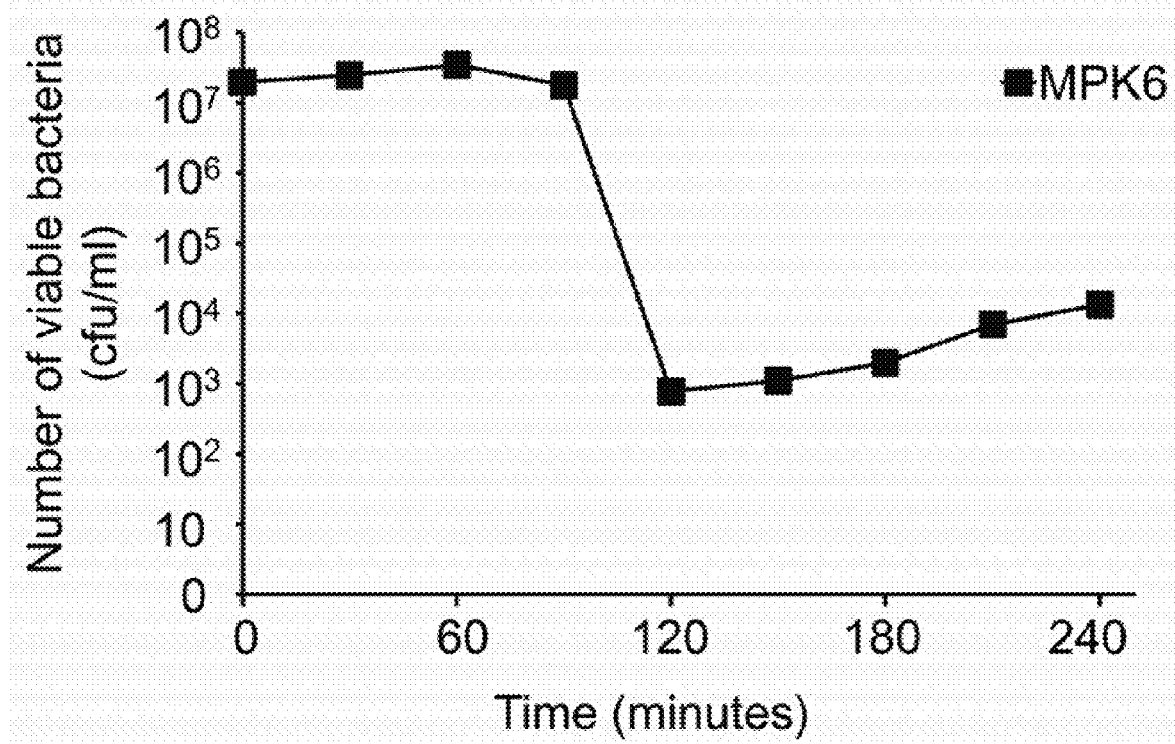
FIG. 3 shows a lytic activity of MPK6 in vitro. The PAO1 culture suspension were mixed with the phage lysate of MPK6 (■) in LB at the MOI of 1 and then incubated further. The number of viable bacteria (CFU) was measured at appropriate dilutions to count about $10^2$ CFU.

The lytic activity of the phage MPK6 was examined based on the single step growth curve in the phage life cycle. *P. aeruginosa* PAO1 cells (~$10^7$ CFU) was incubated in the medium containing MPK6 at multiplicity of infection (MOI) of 1. The number of viable bacteria gradually decreased up to about $10^3$ CFU for MPK6 after 120 min (FIG. 3), demonstrating that the phage has a potent lytic activity towards *P. aeruginosa* PAO1. The capability of growth inhibition in vitro by the phage led the present inventors to further evaluate the antibacterial efficacy against experimental infections (in vivo) caused by *P. aeruginosa*.

Pharmacokinetics of Phage MPK6 in Mouse

Figure 4:
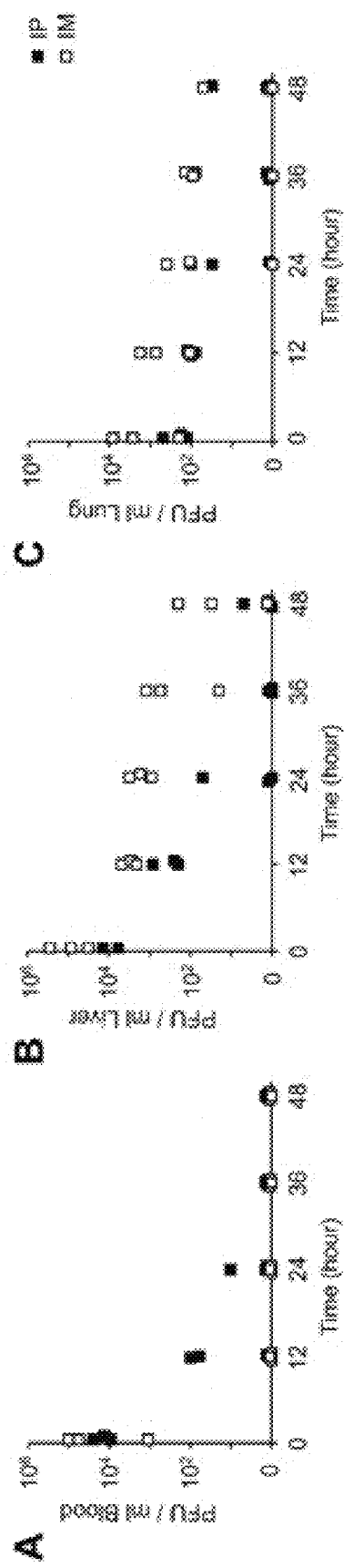
FIG. 4 is pharmacokinetics of MPK6 in mice. Phage samples ($5 \times 10^7$ PFU in PBS) of MPK6 (A, B and C; □ and ■) were administered intraperitoneally (i.p. solid symbols) or intramuscularly (i.m. open symbols) into uninfected mice, respectively. Groups of mice (n=3) were sacrificed at 0.5, 12, 24, 36, and 48 h post-infection and blood (A), liver (B), and lung (C) were extracted and their homogenates were used to measure the PFU per unit volume (ml) as described in Materials and Methods. The PFU/ml is shown in a log scale.

Prior to evaluating the therapeutic efficacy, we examined the pharmacokinetics of both phages to determine which way is the better to deliver phages in mice, between intraperitoenal (i.p.) and intramuscular (i.m.) routes. Phages ($5 \times 10^7$ PFU) were introduced via the i.p. or i.m. route into uninfected mice. Three mice each from groups receiving phage samples i.p. or i.m. were euthanized at 0.5, 12, 24, 36, and 48 h post-infection. The number of phage was enumerated from organs (liver and lung) and blood (per milliliter) (FIG. 4). In each tissue examined, a consistent pattern of the relative PFU levels after administration of the phage by the different routes was observed: i.m.>i.p., which is consistent to the previous study using phage cocktail containing $10^8$ PFU against burn wound infection by *P. aeruginosa* (23). In all conditions, the phages were delivered right after (i.e., 30 min) phage administration. MPK6 was hardly recovered from blood, especially when MPK6 was delivered by the I.m. route (FIG. 4C). These results suggest that *P. aeruginosa* phage (MPK6) has similar pharmacokinetics in mice compared to MPK1 (data not shown).

Therapeutic Efficacy of MPK6 Against Mouse Peritoneal Infection

Figure 5:
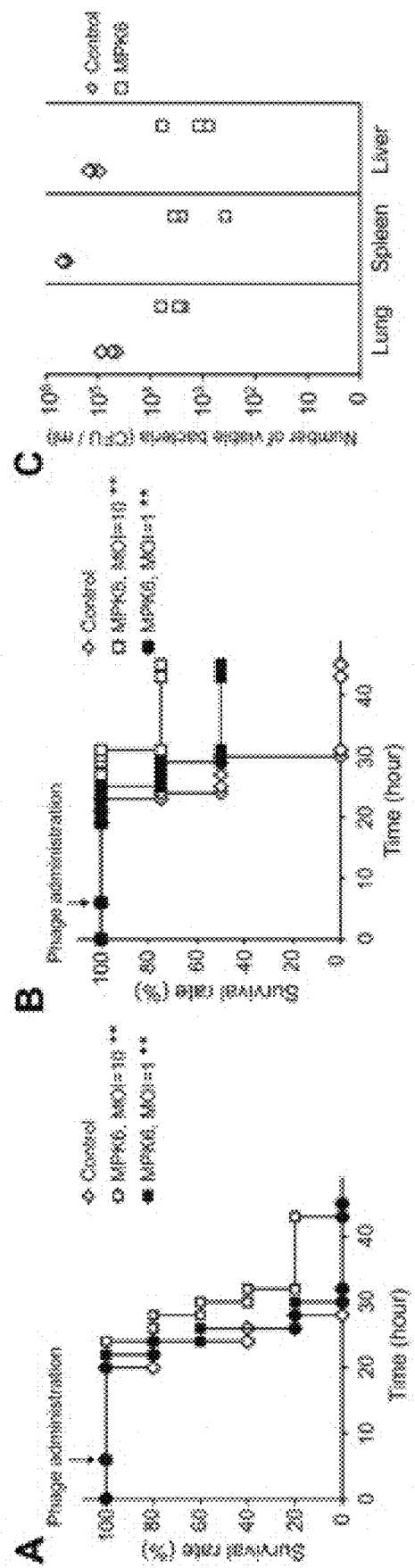
FIG. 5 represents a protective effect of MPK6 in mice.

Phage MPK6 was injected by either i.m. or i.p. route with different doses (at MOI of 1 or 10) of *P. aeruginosa* strain PAO1 after 6 h post-infection. The phage at MOI of 10 rather than at MOI of 1 significantly protected the infected mice compared to the untreated mice (FIGS. 5A and B). No significant protection was observed for MPK6 at MOI of 1 administrated by the i.m. route (FIG. 4A; p=0.316). Despite the better phamarcokinetics of the i.m. administration as in FIG. 4, the i.p. administration displayed the better efficacy for MPK6. It is most likely that the i.p. administration can delivers the phages more directly or effectively to the infection site, since we used the peritonitis model. To verify whether the administration of phages could inhibit the bacterial proliferation, we determined the bacterial loads in mouse organs that include spleen, lung, and liver, since peritonitis is concomitant with bacterial infiltration at the liver of infected animals (5). The organ samples were obtained from live animals at 24 h post-infection. As shown in FIG. 5C, Treatment of the phage could significantly reduce the bacterial loads; MPK6 treatment could reduce the bacterial burdens by about 2 logs in liver from live mice at 24 h post-infection. These results suggest that the phage are highly effective to control *P. aeruginosa*-induced peritonitis by inhibiting bacterial proliferation in vivo.

Pharmacokinetics and Therapeutic Efficacy of Phage MPK1 and MPK6 in a Melanogaster

*D. melanogaster* systemic infection model is well established to study the bacterial virulence mechanisms and needs a very small numbers of *P. aeruginosa* cells (50-200 CFU) to infect, compared to the murine peritonitis model ($10^7$ CFU). It causes death within 48 h, as a result of systemic infection by bacterial proliferation up to about $10^7$ CFU under our optimized experimental conditions (18, 20). To establish the *D. melanogaster* model to evaluate phage therapy against *P. aeruginosa*, we exploited feeding phages to a group (n=50) of flies in a fly vial by overlaying the phage samples containing $5 \times 10^7$ PFU onto a fly vial containing 2.5 ml of corn-meal medium.

Figure 6:
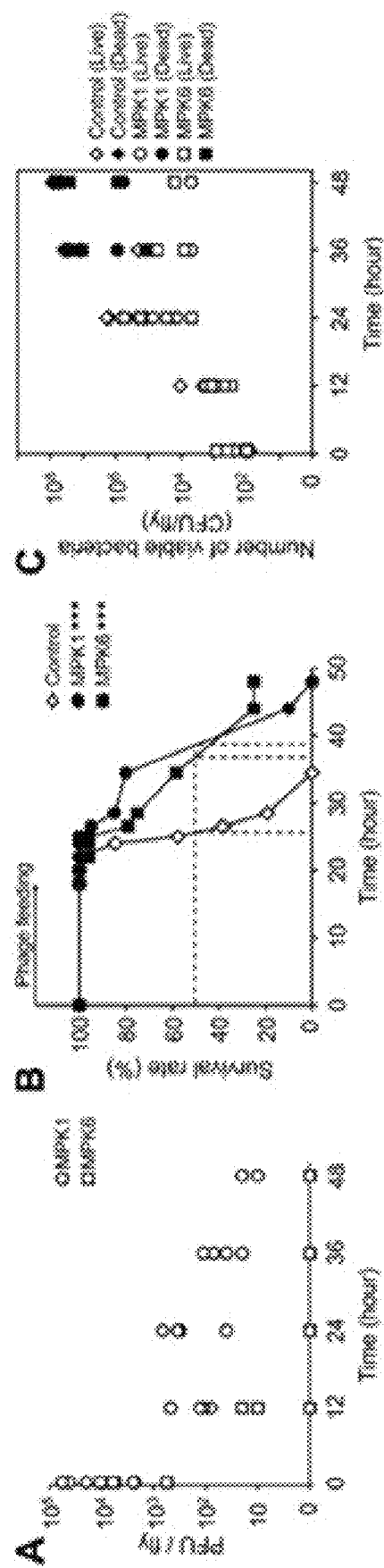
FIG. 6 represents a bacteriophage therapy against *D. melanogaster* systemic infection.

We first examined the pharmacokinetics of both phages which could be orally administered to *D. melanogaster*, in order to assess their potential toxicity as well as their persistence in fly tissues. Uninfected flies were fed with either of both phages ($5\times10^7$ PFU) and transferred to a new medium without phage feeding. As shown in FIG. 6A, phages were recovered from fed flies, indicating that phages might be successfully administered by the overlay on top of a medium. About $10^4$ PFU of both phages were transferred by only 12 h feeding. As well, MPK1 was maintained for upto 48 h after transfer to a new medium, although the PFU was gradually decreased by about 3 logs at 48 h. Interestingly, MPK6 was poorly recovered and disappeared before 12 h without bacterial infection after transfer to a new medium. Furthermore, both phages were not toxic at all by 12 h feeding. No fly died even with phage feeding for more than 72 h (data not shown). These results suggest that phage feeding can be exploited to administer phages for phage therapy for *D. melanogaster* infection.

Next the antibacterial efficacy of both phages was evaluated, based on their protective effects from PAO1-induced mortality and proliferaction in *D. melanogaster* infection model. Phages MPK1 and MPK6 were administered by overlaying $5\times10^7$ PFU on a fly vial to accommodate 50 PAO1-infected flies (i.e., feeding $10^6$ phage for a fly). Both phages significantly protected the infected flies compared to the flies without phage feeding (FIG. 6B). The similar efficacy was observed for both phages (p=0.637), although the better pharmacokinetics of MPK1 was observed in fly tissues.

We examined the protective effect on the bacterial proliferation in the fly tissue by phage feeding. As shown in FIG. 6C, MPK6 and, to the larger extent, MPK1 inhibited the bacterial proliferation in this infection condition. Since *P. aeruginosa* reaches $10^7$ CFU (i.e., by 5 log increase), when the infected flies died (20), more than 2 log inhibition could be sufficient to resist PAO1-induced killing, when flies started to die. These results suggest that both phages are highly effective to control *P. aeruginosa* induced *D. melanogaster* killing by inhibiting bacterial proliferation in vivo.

Discussion

Phage therapy was first introduced more than 80 years ago (14) but the possibility of bacterial resistance to phage was emerged an obstacle in the development of an effective phage therapy system (21). However, Smith and colleagues previously showed that infections produced by phage-resistant mutants of an enteropathogenic strain *E. coli* and their parents could be successfully controlled with mutant phage derived from phage that had been active against the parental bacteria (31, 32). Even if the bacteria acquire phage resistance, new mutant phage that acts effectively against these bacteria are readily available to researchers, for example from sewage treatment plants and hospital effluents, or by laboratory manipulation (typically UV exposure) (22). It is already possible to prepare a mixture of different strains of phages (i.e., phage cocktail) that would prevent the emergence of a resistant strain during phage treatment. Thus the phage therapy is one of the most important and handy modalities that can control the bacterial infections in the era of antibiotic resistance.

Several cases of the phage therapy against the experimental infections by *P. aeruginosa* in mice were reported, which include gut-derived sepsis and burn wound infections (23, 36). A recent study on pyocin therapy was based on mouse peritonitis model (29). All those experimental infection models appear relevant considering that the complicated pathophysiology caused by *P. aeruginosa* infections. More importantly, *P. aeruginosa* is a multi-host pathogen that can intoxicate phylogenetically diverse hosts including mammals, insects, worms, and plants, involving a distinct set of virulence factors. Thus various infection models should be exploited to evaluate and confirm the antibacterial efficacy of antimicrobial agents. We tested for the acute lung infection in mice by intranasal administration of *P. aeruginosa* cells to evaluate the antibacterial efficacy of MPK1, which was either intraperitoneally or intramusculary administered. However, the lung infection-derived mortality was not prevented at all, most likely due to the lower phage delivery in the lung, compared to the blood and the liver by those administration routes, which needs to be further optimized. Thus, the differential infection conditions caused by *P. aeruginosa* may necessitate the differential administration conditions based on the pharmacokinetic properties of therapeutic phages to ensure the optimal antibacterial efficacy.

Although it is clear that the current phage therapy mostly employing lytic phages involves the bacteriolytic activity of the phages, but some lysogenic phage could be potentially considered in a near future as the alternative modality to control the virulence. Zegans et a/reported that a *P. aeruginosa* temperate phage, MS3 modulated the group behavior including swarming motility and biofilm formation by interacting with the host proteins as a lysogenic form (40). Since the group behaviors such as biofilm formation and quorum sensing are crucial in the virulence and/or survival mechanisms of *P. aeruginosa* (11), the possibility of phage therapy exploiting lysogenic phages with such properties needs to be tested using a live-animal infection model. The major obstacle of using temperate phages for antibacterial therapy may be that they can integrate themselves relatively randomly into the host chromosome, potentially leading to the unexpected consequences regarding virulence traits of the bacteria (24). However, there has been no direct evidence for that and we could not expect whether the dynamic and complicated interactions between the temperate or lysogenic phages and the bacteria within the infected hosts are either beneficial or detrimental to each party. Thus, we could carefully begin to evaluate the antibacterial efficacy of temperate phages as well as lytic phages or the mixture of both kinds, under concerns regarding the potential side effects resulted from unpredictable mutation (for temperate phages) and cytolysis-derived endotoxin generation (for lytic phages).

The major obstacle of using temperate phages for antibacterial therapy may be that they can integrate themselves relatively randomly into the host chromosome, potentially leading to the unexpected consequences regarding virulence traits of the bacteria (24). However, there has been no direct evidence for that and we could not expect whether the dynamic and complicated interactions between the temperate or lysogenic phages and the bacteria within the infected hosts are either beneficial or detrimental to each party. Thus, we could carefully begin to evaluate the antibacterial efficacy of temperate phages as well as lytic phages or the mixture of both kinds, under concerns regarding the potential side effects resulted from unpredictable mutation (for temperate phages) and cytolysis-derived endotoxin generation (for lytic phages), which can be facilitated by the extensive use of non-mammalian live animal infections like *C. elegans* and *D. melagnoaster*. The further optimization of *D. melanogaster* model to evaluate the antibacterial efficacy of various phages against *P. aeruginosa* infection will enlarge our insights into antimicrobial therapy and provide a platform to specifically modulate the interface between bacterial virulence and host immunity.

One of the meaningful aspects of the present study is that we established a new therapeutic animal model to evaluate the antibacterial activity in vivo using a non-mammalian model host, *Drosophila* melanogaster. We are currently investigating how phages are administered and where they are specifically localized within fly tissues to optimize this model for further studies. In recent studies, a non-mammalian live-animal infection model using a nematode, *Caenorhabditis elegans* infection model has been successfully exploited for high through-put screens to isolate new antimicrobial compounds against *Enterococcus faecalis* or *Candida albicans* (9, 25). A major advantage using non-mammalian model hosts is that the research costs (mammalian animals and space etc) and, more importantly, the experimental scale can be significantly reduced, since the small size of the non-mammalian model animals requires far less space and amount of pathogens and antimicrobials for the experimental settings, which in turn enables the high-throuput analysis from the chemical libraries as well. Another great advantage of such live-animal infection model is that new antimicrobial compounds can be isolated, which do not inhibit the growth of the target microorganisms, but attenuate the virulence pathways and/or enhance the host immune response. Although it is clear that the current phage therapy mostly employing lytic phages involves the bacteriolytic activity of the phages, but some lysogenic phage could be potentially considered in a near future as the alternative modality to control the virulence. Zegans et al reported that a *P. aeruginosa* temperate phage, DMS3 modulated the group behavior including swarming motility and biofilm formation by interacting with the host proteins as a lysogenic form (39). Since the group behaviors such as biofilm formation and quorum sensing are crucial in the virulence and/or survival mechanisms of *P. aeruginosa* (11), the possibility of phage therapy exploiting lysogenic phages with such properties needs to be tested using a live-animal infection model.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Ackermann, H. W. 2001. Frequency of morphological phage descriptions in the year 2000. Brief review. Arch Virol 146:843-57.
2. Ackermann, H. W. 1998. Tailed bacteriophages: the order caudovirales. Adv Virus Res 51:135-201.
3. Alisky, J., K. Iczkowski, A. Rapoport, and N. Troitsky. 1998. Bacteriophages show promise as antimicrobial agents. J Infect 36:5-15.
4. Aronoff, S. C., M. M. Olson, M. W. Gauderer, M. R. Jacobs, J. L. Blumer, and R. J. Izant, Jr. 1987. *Pseudomonas aeruginosa* as a primary pathogen in children with bacterial peritonitis. J Pediatr Surg 22:861-4.
5. Barekzi, N. A., K. A. Poelstra, A. G. Felts, I. A. Rojas, J. B. Slunt, and D. W. Grainger. 1999. Efficacy of locally delivered polyclonal immunoglobulin against *Pseudomonas aeruginosa* peritonitis in a murine model. Antimicrob Agents Chemother 43:1609-15.
6. Bradley, D. E. 1973. The length of the filamentous *Pseudomonas aeruginosa* bacteriophage Pf. J Gen Virol 20:249-52.
7. Bradley, D. E. 1973. A pilus-dependent *Pseudomonas aeruginosa* bacteriophage with a long noncontractile tail. Virology 51:489-92.
8. Bradley, D. E. 1967. Ultrastructure of bacteriophage and bacteriocins. Bacteriol Rev 31:230-314.
9. Breger, J., B. B. Fuchs, G. Aperis, T. I. Moy, F. M. Ausubel, and E. Mylonakis. 2007. Antifungal chemical compounds identified using a *C. elegans* pathogenicity assay. PLoS Pathog 3:e18.
10. Hagens, S., A. Habel, U. von Ahsen, A. von Gabain, and U. Blasi. 2004. Therapy of experimental pseudomonas infections with a nonreplicating genetically modified phage. Antimicrob Agents Chemother 48:3817-22.
11. Hausner, M., and S. Wuertz. 1999. High rates of conjugation in bacterial biofilms as determined by quantitative in situ analysis. Appl Environ Microbiol 65:3710-3.
12. Heo, Y.-J., I.-Y. Chung, K. B. Choi, and Y.-H. Cho. 2007. R-type pyocin is required for competitive growth advantage between *Pseudomonas aeruginosa* strains. J Microbiol Biotechnol 17:180-5.
13. Heo, Y.-J., I.-Y. Chung, K. B. Choi, G. W. Lau, and Y.-H. Cho. 2007. Genome sequence comparison and superinfection between two related *Pseudomonas aeruginosa* phages, D3112 and MP22. Microbiology 153:2885-95.
14. Ho, K. 2001. Bacteriophage therapy for bacterial infections. Rekindling a memory from the pre-antibiotics era. Perspect Biol Med 44:1-16.
15. Jarrell, K. F., and A. M. Kropinski. 1981. *Pseudomonas aeruginosa* bacteriophage phi PLS27-lipopolysaccharide interactions. J Virol 40:411-20.
16. Johnson, C. C., J. Baldessarre, and M. E. Levison. 1997. Peritonitis: update on pathophysiology, clinical manifestations, and management. Clin Infect Dis 24:1035-45; quiz 1046-7.
17. Juergensen, P. H., F. O. Finkelstein, R. Brennan, S. Santacroce, and M. J. Ahern. 1988. *Pseudomonas* peritonitis associated with continuous ambulatory peritoneal dialysis: a six-year study. Am J Kidney Dis 11:413-7.
18. Kim, S.-H., S.-Y. Park, Y.-J. Heo, and Y.-H. Cho. 2008. *Drosophila melanogaster*-based screening for multihost virulence factors of *Pseudomonas aeruginosa* PA14 and identification of a virulence-attenuating factor, HudA. Infect Immun 76:4152-62.
19. Krothapalli, R., W. B. Duffy, C. Lacke, W. Payne, H. Patel, V. Perez, and H. O, Senekjian. 1982. *Pseudomonas* peritonitis and continuous ambulatory peritoneal dialysis. Arch Intern Med 142:1862-3.
20. Lee, J.-S., Y.-J. Heo, J. K. Lee, and Y.-H. Cho. 2005. KatA, the major catalase, is critical for osmoprotection and virulence in *Pseudomonas aeruginosa* PA14. Infect Immun 73:4399-403.
21. Lowbury, E. J., and A. M. Hood. 1953. The acquired resistance of *Staphylococcus aureus* to Bacteriophage. J Gen Microbiol 9:524-35.
22. Matsuzaki, S., M. Rashel, J. Uchiyama, S. Sakurai, T. Ujihara, M. Kuroda, M. Ikeuchi, T. Tani, M. Fujieda, H. Wakiguchi, and S. Imai. 2005. Bacteriophage therapy: a revitalized therapy against bacterial infectious diseases. J Infect Chemother 11:211-9.
23. McVay, C. S., M. Velasquez, and J. A. Fralick. 2007. Phage therapy of *Pseudomonas aeruginosa* infection in a mouse burn wound model. Antimicrob Agents Chemother 51:1934-8.
24. Mizuuchi, K., and R. Craigie. 1986. Mechanism of bacteriophage mu transposition. Annu Rev Genet. 20:385-429.
25. Moy, T. I., A. R. Ball, Z. Anklesaria, G. Casadei, K. Lewis, and F. M. Ausubel. 2006. Identification of novel antimicrobials using a live-animal infection model. Proc Natl Acad Sci USA 103:10414-9.

26. Pruitt, B. A., Jr., A. T. McManus, S. H. Kim, and C. W. Goodwin. 1998. Burn wound infections: current status. World J Surg 22:135-45.
27. Rocchetta, H. L., Burrows, L. L. and Lam, J. S. 1999. Genetics of O-Antigen Biosynthesis in *Pseudomonas aeruginosa*. Microbiol Mol Reviews 62:523-553
28. Rosenfeld, M., B. W. Ramsey, and R. L. Gibson. 2003. *Pseudomonas* acquisition in young patients with cystic fibrosis: pathophysiology, diagnosis, and management. Curr Opin Pulm Med 9:492-7.
29. Scholl, D., and D. W. Martin, Jr. 2008. Antibacterial efficacy of R-type pyocins towards *Pseudomonas aeruginosa* in a murine peritonitis model. Antimicrob Agents Chemother 52:1647-52.
30. Slopek, S., B. Weber-Dabrowska, M. Dabrowski, and A. Kucharewicz-Krukowska. 1987. Results of bacteriophage treatment of suppurative bacterial infections in the years 1981-1986. Arch Immunol Ther Exp (Warsz) 35:569-83.
31. Smith, H. W., and M. B. Huggins. 1983. Effectiveness of phages in treating experimental *Escherichia coli* diarrhoea in calves, piglets and lambs. J Gen Microbiol 129:2659-75.
32. Smith, H. W., M. B. Huggins, and K. M. Shaw. 1987. The control of experimental *Escherichia coli* diarrhoea in calves by means of bacteriophages. J Gen Microbiol 133: 1111-26.
33. Speert, D. P., M. E. Campbell, D. A. Henry, R. Milner, F. Taha, A. Gravelle, A. G. Davidson, L. T. Wong, and E. Mahenthiralingam. 2002. Epidemiology of *Pseudomonas aeruginosa* in cystic fibrosis in British Columbia, Canada. Am J Respir Crit. Care Med 166:988-93.
34. Steinstraesser, L., Y. Oezdogan, S. C. Wang, and H. U. Steinau. 2004. Host defense peptides in burns. Burns 30:619-27.
35. Summers, W. C. 2001. Bacteriophage therapy. Annu Rev Microbiol 55:437-51.
36. Summers, W. C. 1999. Felix d'Herelle and the origins of molecular biology. Yale University Press, New Haven, Conn.
37. Watanabe, R., T. Matsumoto, G. Sano, Y. Ishii, K. Tateda, Y. Sumiyama, J. Uchiyama, S. Sakurai, S. Matsuzaki, S. Imai, and K. Yamaguchi. 2007. Efficacy of bacteriophage therapy against gut-derived sepsis caused by *Pseudomonas aeruginosa* in mice. Antimicrob Agents Chemother 51:446-52.
38. Weinstein, W. M., A. B. Onderdonk, J. G. Bartlett, and S. L. Gorbach. 1974. Experimental intra-abdominal abscesses in rats: development of an experimental model. Infect Immun 10:1250-5.
39. Yokota, S., T. Hayashi, and H. Matsumoto. 1994. Identification of the lipopolysaccharide core region as the receptor site for a cytotoxin-converting phage, phi CTX, of *Pseudomonas aeruginosa*. J Bacteriol 176:5262-9.
40. Zegans, M. E., J. C. Wagner, K. C. Cady, D. M. Murphy, J. H. Hammond, and G. A. O'Toole. 2008. Interaction between bacteriophage DMS3 and host CRISPR region inhibits group behaviors of *Pseudomonas aeruginosa*. J Bacteriol 191:210-219.

The invention claimed is:

1. An isolated bacteriophage MPK6 as deposited with the Korean Culture Center of Microorganisms under Accession No. KCCM 11044P having a lytic activity to *Pseudomonas aeruginosa*.

2. A pharmaceutical composition for treating a *Pseudomonas aeruginosa* infection disease, comprising: (a) a therapeutically effective amount of the bacteriophage according to claim 1; and (b) a pharmaceutically acceptable carrier.

3. The composition according to claim 2, wherein the *Pseudomonas aeruginosa* infection disease comprises cystic fibrosis, otitis media, keratitis, endophthalmitis, bacteremia, burn wound infection, pneumonia, meningitis, peritonitis or sepsis.

4. The composition according to claim 3, wherein the *Pseudomonas aeruginosa* infection disease comprises pneumonia, meningitis, peritonitis or sepsis.

* * * * *